US00PP28244P3

(12) United States Plant Patent
Kordes

(10) Patent No.: US PP28,244 P3
(45) Date of Patent: Aug. 8, 2017

(54) CLIMBING ROSE PLANT NAMED 'KORCASEIPP'

(50) Latin Name: *Rosa hybrida*
Varietal Denomination: KORcaseipp

(71) Applicant: W. Kordes Söhne Rosenschulen GmbH & Co. KG, Klein Offenseth-Sparrieshoop (DE)

(72) Inventor: Tim-Hermann Kordes, Klein Offenseth-Sparrieshoop (DE)

(73) Assignee: W. Kordes Söhne Rosenschulen GmbH & Co. KG, Klein Offenseth-Sparrieshoop (DE)

( * ) Notice: Subject to any disclaimer, the term of this patent is extended or adjusted under 35 U.S.C. 154(b) by 139 days.

(21) Appl. No.: 14/545,934

(22) Filed: Jul. 8, 2015

(65) Prior Publication Data

US 2016/0014937 P1 Jan. 14, 2016

Related U.S. Application Data

(60) Provisional application No. 61/998,921, filed on Jul. 11, 2014.

(51) Int. Cl.
*A01H 5/02* (2006.01)

(52) U.S. Cl.
USPC ..... Plt./113

(58) Field of Classification Search
USPC ..... Plt./101, 109, 113
See application file for complete search history.

(56) References Cited

PUBLICATIONS

Help Find Me: Roses, Clematis and Peonies website, citation for 'Korcaseipp'. http://www.helpmefind.com/gardening/pl.php?n=92016. Accessed Jan. 11, 2017. 1 page.*

* cited by examiner

*Primary Examiner* — Susan McCormick Ewoldt
*Assistant Examiner* — Karen Redden

(57) ABSTRACT

'KORcaseipp' is a new and distinct variety of *Rosa hybrida* which is characterized by the combination of a climbing growth habit, an abundance of large and very double-type flowers which are pastel apricot in color and also attractive foliage with very good disease resistance. The new variety propagates successfully by grafting and by stem cuttings and has shown to be uniform and stable in the resulting generations from asexual propagation.

1 Drawing Sheet

Latin name of genus and species: The Latin name of the genus and species of the novel variety disclosed herein is *Rosa hybrida.*

Variety denomination: The inventive variety of *Rosa hybrida* disclosed herein has been given the variety denomination 'KORcaseipp'.

BACKGROUND OF THE INVENTION

The present invention relates to a new and distinct *Rosa hybrida*, climbing rose cultivar, of the market class PLT/109.

Parentage: The *Rosa hybrida* variety 'KORcaseipp' is the result of a controlled cross-pollination breeding program carried out by the inventor in Offenseth-Sparrieshoop, Germany. The objective of the said breeding program was to create a new and distinct rose plant with unique qualities, such as:

1. Uniform growth and flowering;
2. Abundant attractive, recurrent flowers;
3. Attractive and abundant foliage; and
4. Resistance to diseases encountered in landscapes and gardens.

This combination of qualities is not present in prior rose cultivars known to the inventor. These objectives have been substantially achieved and in that distinguish 'KORcaseipp' from all other varieties known to the inventor.

'KORcaseipp' is a seedling selection which resulted from the controlled pollination of two proprietary *Rosa hybrida* cultivars, developed and owned by the same inventor, during the summer of 1998. Said cross-pollination was made between the seed parent, *Rosa hybrida* 'KORkinteral' (unpatented), and the pollen parent, *Rosa hybrida* 'KORpastato' (unpatented).

As part of a rose development program, Tim-Hermann Kordes germinated seeds from the aforementioned hybridization during the winter of 1998 and conducted evaluations and observations on the resulting seedlings in a controlled environment in Offenseth-Sparrieshoop, Germany. The resulting seedlings exhibited distinctive physical and biological characteristics. The new rose plant was selected as a single plant in May of 1999 from the seedling beds due to its superior characteristics and asexually propagated for further evaluation. This new and distinctive rose variety was given the name 'KORcaseipp'.

Asexual Reproduction: The first asexual propagation of 'KORcaseipp' was done by budding in July of 1999 at the inventor's nursery in Offenseth-Sparrieshoop, Germany and has since been successfully asexually propagated by stem cuttings and grafting in Jackson County, Oreg. These initial and other subsequent propagations conducted in controlled environments demonstrate that 'KORcaseipp' reproduces true to type in successive generations of asexual reproduction.

SUMMARY OF THE INVENTION

The following characteristics have been repeatedly observed and represent the distinguishing characteristics of the new *Rosa hybrida* cultivar 'KORcaseipp'. These traits, in combination, distinguish 'KORcaseipp' as a new and distinct cultivar.

1. *Rosa hybrida* 'KORcaseipp' exhibits a climbing growth habit; and
2. *Rosa hybrida* 'KORcaseipp' exhibits an abundance of flowers; and
3. *Rosa hybrida* 'KORcaseipp' exhibits a very-double flower type; and
4. *Rosa hybrida* 'KORcaseipp' exhibits a large flower size; and
5. *Rosa hybrida* 'KORcaseipp' exhibits a pastel apricot flower color, at anthesis; and
6. *Rosa hybrida* 'KORcaseipp' exhibits semi-glossy foliage; and
7. *Rosa hybrida* 'KORcaseipp' exhibits very good disease resistance.

BRIEF DESCRIPTION OF THE DRAWING

The accompanying color drawing shows as true as is reasonably possible to obtain in color photographs of this type, the typical characteristics of the buds, sepals, reproductive organs, flowers, leaves, prickles, and stems of 'KORcaseipp', taken from plants of one and one half years of age.

DETAILED BOTANICAL DESCRIPTION

The following is a detailed botanical description of a new and distinct variety of *Rosa hybrida* known as KORcaseippi, based upon observations of plants of one and one half years of age growing in September of 2014 at a nursery in Jackson County, Oreg.

Those skilled in the art will appreciate that certain characteristics will vary with older or, conversely, with younger plants. 'KORcaseipp' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2001 edition except where common terms of color are used.

A botanical description of 'KORcaseipp' and comparisons with other varieties of *Rosa hybrida* are provided below.

General plant description:

*Growth rate*.—Moderately vigorous.

*Growth habit*.—Upright; climbing.

*Mature dimensions*.—Approximately 220 cm tall and 75 cm wide.

*Cold hardiness*.—To date, the variety has been grown successfully in USDA Hardiness Zone 6.

*Propagation*.—Grafting and stem cuttings.

*Disease resistance*.—Very good resistance to powdery mildew (*Sphaerotheca pannosa*), blackspot (*Diplocarpon rosae*), rust (*Phragmidium tuberculatum*) and downy mildew (*Peronospora sparsa*) diseases under normal growing conditions in Jackson County, Oreg.

Root system:

*Type*.—Fibrous root system with many root hairs.

*Branching*.—Freely branched.

*Density*.—Moderately dense rooting.

*Distribution*.—Roots distributed uniformly throughout the soil profile, from shallow to deep.

*Color*.—Orange-white, nearest to RHS 159D.

Stems:

*Stem color*.—Immature stems are Yellow-Green Group 144A; mature stems are also Yellow-Green Group 144A.

*Intonations*.—Intonations of immature stems are Red-Purple Group 59B and mature stems are Red-Purple Group 58A.

*Stem surface texture*.—The surfaces of both immature and mature stems are smooth.

*Prickles*.—Incidence — Present; average of 10 to 15 large prickles and 10 small prickles per each 10 cm of stem on young wood. Only small prickles persisting on mature wood. Size — Average length of large prickles is 5 to 9 mm and the average length of the small prickles is 1 to 3 mm. Immature prickle color — Yellow-Green Group 145C. Mature prickle color — Yellow-Green Group 145C; senescing to Greyed-Orange Group 165C. Anthocyanin — Red-Purple Group 59B on immature prickles and Red-Purple Group 58A on mature prickles. Shape — Deeply concave. Texture — Smooth.

Leaves:

*Arrangement*.—Imparipinnate compound leaves; mature axillary leaves consisting of 7 leaflets.

*Attachment*.—Petiolate.

*Dimensions*.—120 to 160 mm long and 85 to 115 mm wide.

*Abundance*.—Average.

*Stipules*.—Size — 15 mm long and 5 mm wide. Stipule color — Yellow-Green Group 146B; Yellow-Green Group 146D on adaxial surface of the midrib. Anthocyanin — Not Observed. Stipitate glands — Abundant on margins and abaxial surface. Margins — Glandular toothed. Texture, adaxial surface — Glabrous. Texture, abaxial surface — Papillate. Apex — Apiculate. Base — Winged.

*Petiole*.—Length — Average 20 to 25 mm. Diameter — Average 1 to 2 mm. Petiole color, adaxial surface — Yellow-Green Group 146B. Petiole color, abaxial surface — Yellow-Green Group 146B. Margins — Entire; stipitate; glands present. Anthocyanin — Not Observed. Prickles — Typically one small prickle on the abaxial surface. Stipitate glands — Limited number of stipitate glands present on margins and abaxial surface. Texture — Papillate. Fine hairs on midrib.

*Rachis*.—Length — Average 20 to 25 mm. Diameter — Average 1 to 2 mm. Color — Yellow-Green Group 146A. Anthocyanin — Not observed. Margins — Entire. Stipitate glands present. Prickles — A few small prickles underneath. Stipitate glands — Limited numbers of stipitate glands on margins and underneath. Texture — Papillate.

*Leaflets*.—Quantity — Normally 7 leaflets on normal leaves in middle of the stem. Dimensions — Average size of the terminal leaflet is 50 to 65 mm long and 30 to 40 mm wide. Shape — Ovate. Apex — Acute.

Base — Obtuse. Margins — Serrated. Texture, adaxial surface — Semi-glossy to glossy and leathery. Texture, abaxial surface — Matte and rugose. Pubescence — Glabrous. Juvenile foliage color, adaxial surface — Yellow-Green Group 146A. Juvenile foliage color, abaxial surface — Yellow-Green Group 146B. Mature foliage color, abaxial surface — Green Group 139A. Mature foliage color, abaxial surface — Green Group 137C. Anthocyanin intonation — Greyed-Purple Group 183A. Covers most immature foliage; present on margins, midrib and abaxial surface of juvenile foliage. Absent on mature foliage. Venation — Reticulate. Petiolule — Dimensions — 4 mm long and 2 mm in diameter. Petiolule color, adaxial surface — Yellow-Green Group 146D. Anthocyanin present along the margins, corresponding to Greyed-Purple Group 183A. Petiolule color, abaxial surface — Yellow-Green Group 146D. Prickles — Few are present on the abaxial surface. Texture — Coriaceous; stipitate glands are present along margins.

Inflorescence:

*Inflorescence type*.—Panicle.

*Blooming habit*.—Recurrent.

*Quantity of flowers*.—1 to 5, on average.

*Size*.—20 cm tall and 15 cm wide, on average.

*Peduncle*.—Surface — Lacking fine hairs and stipitate glands. Length — 20 to 70 mm average length. Diameter — 3 to 4 mm average diameter. Color — Yellow-Green Group 144A. Intonations — Red-Purple Group 58A. Strength — Strong. Texture — Glabrous.

Bud:

*Bud form*.—Pointed ovoid.

*Size*.—Upon opening, 25 mm in length from base of receptacle to distal end of bud and 17 mm diameter at its widest point.

*Color, as sepals first unfold*.—Red Group 36D, with intonations of Red Group 50B.

*Color when one-quarter open, upper surface of petal*.—Marginal zone — White Group N155C. Middle zone — White Group N155C. Basal zone — Orange Group 27A.

*Color when one-quarter open, lower surface of petal*.—Marginal zone — White Group N155D. Middle zone — White Group N155D. Basal zone — Red Group 49B.

Flower:

Pedicel:

*Surface*.—Lacking fine hairs. Limited numbers of stipitate glands present.

*Length*.—25 to 55 mm, on average.

*Diameter*.—3 to 4 mm, on average.

*Color*.—Yellow-Green Group 144A.

*Intonations*.—Red-Purple Group 58A.

*Strength*.—Somewhat strong.

*Texture*.—Papillate.

Sepals:

*Color, adaxial surface*.—Green Group 138A and 138B.

*Color, abaxial surface*.—Yellow-Green Group 144A.

*Intonations*.—Red-Purple 58A on margins and upper surface occasionally.

*Size*.—20 to 30 mm long and 8 to 10 mm wide, on average.

*Shape*.—Moderate foliaceous appendages on 3 of the 5 sepals.

*Apex*.—Apiculate.

*Base*.—Flat at union with receptacle.

*Quantity*.—Five.

*Texture, adaxial surface*.—Hoary.

*Texture, abaxial surface*.—Leathery.

*Margins*.—Entire, hoary.

*Stipitate glands*.—Lacking.

Corolla:

*Corolla habit*.—Very Double.

*General shape of corolla*.—Round.

*Shape of corolla when viewed from the side*.—Upon opening, upper portion — Flat. Upon opening, lower portion — Convex. Open flower, upper portion — Flat. Open flower, lower portion — Flat.

*Dimensions*.—Large for a climbing rose. When open, the average flower diameter is 90 mm and the average flower height is 30 mm.

*Fragrance*.—Moderate.

*Duration*.—On the plant 6 days. Senesced petals drop away cleanly.

*Petals*.—Petal Arrangement — Rosette. Petal Count — Approximately 130 to 140 petals under normal conditions. Petal Reflex — Petals reflex somewhat. Reflex occurs one by one. Petal Margin — Entire; ruffled. Petal Shape — Obovate to cuneate. Apex — Obtuse. Base — Cuneate. Dimensions — Approximately 25 to 50 mm long and 15 to 55 mm wide. Texture, inner surface — Smooth. Texture, outer surface — Smooth. Color, upon opening — Outermost petals, outer surface — Marginal zone — White Group N155C. Middle zone — Orange Group 27C. Basal zone — Red Group 37A. Outermost petals, inner surface — Marginal zone — White Group N155D. Middle zone — Orange-White Group 1598. Basal zone — Yellow-Orange Group 20D. Innermost petals, outer surface — Marginal zone — Red Group 36A. Middle zone — Red Group 36A. Basal zone — Red Group 37B. Innermost petals, inner surface — Orange Group 27A. Color upon opening, basal petal spots — Basal petal spot, outermost petals — Outer surface — Yellow Group 2A. Inner surface — Yellow Group 3A. Basal petal spot, innermost petals — Outer surface — Yellow Group 3A. Inner surface — Yellow Group 3A. Color after opening — Outermost petals, outer surface — Marginal zone — White Group N155D. Middle zone — White Group N155D. Basal zone — Red Group 36C. Outermost petals, inner surface — Marginal zone — White Group N155D. Middle zone — White Group N155D. Basal zone — Yellow-Orange Group 19D. Innermost petals, outer surface — Orange Group 27D. Innermost petals, inner surface — Orange-White Group 159D. Color after opening, basal petal spots — Basal petal spot after opening, outermost petals — Outer surface — Green-Yellow Group 1 C. Inner surface — Green-Yellow Group 1 D. Basal petal spot after opening, innermost petals — Outer surface — Yellow Group 2B. Inner surface — Yellow Group 2B. General Tonality — On open flower Orange Group 27B. No change in the general tonality at the end of the 4th day. Afterwards, general tonality is White Group N155D.

*Petaloids*.—Quantity — Approximately 40 to 50 petaloids per flower. Dimensions — Approximately 10 to 20 mm long and 5 to 10 mm wide. Color, inner surface — Yellow-Orange Group 19D. Color, outer surface — Orange Group 27B. Texture, inner surface — Smooth. Texture, outer surface — Smooth. Margins — Entire, emarginate and indented petaloid margins observed. Shape — Highly variable, most commonly obovate. Apex — Obtuse. Base — Attenuate.

Reproductive organs:

Stamens:

*Quantity*.—Approximately 5 to 15, on average, and irregularly arranged around the styles.

*Anthers*.—Shape — Reniform. Dimensions — 2 mm long and 1 mm wide, on average. Color — Greyed-Orange Group 163B. Pollen — Generally present. Pollen Color — Greyed-Orange Group 165A.

*Filaments*.—Color — Yellow Group 3C. Length — 5 mm.

Pistils:

*Quantity*.—Approximately 50 present.

*Stigmas*.—Location — Outermost stigmas slightly superior in position to anthers. Innermost stigmas slightly inferior in position to anthers. Color — Greyed-Red Group 179C. Size — Approximately 1 mm in diameter.

*Styles*.—Length — About 4 to 8 mm long. Color — Yellow Group 4B. Intonations — Red Group 45B.

*Receptacle*.—Shape — Urn-shaped. Dimensions — Approximately 10 to 12 mm high and 8 to 10 mm wide. Surface — Glaucous, with limited numbers of fine hairs. Color — Yellow-Green Group 144A. Texture — Smooth.

Hips and seed formation:

*Hip*.—Attitude — Upright to slightly nodding. Shape — Globular. Dimensions — 18 to 30 mm long and 20 to 25 mm wide. Texture — Smooth. Color — Greyed-purple, RHS 183A.

*Seed*.—Not observed.

Comparisons with the Parents

The new rose plant may be distinguished from its seed parent, *Rosa hybrida* 'KORkinteral', by the following combination of characteristics:

1. 'KORkinteral' has an amber yellow flower color, whereas 'KORcaseipp' has a pastel apricot flower color.
2. 'KORkinteral' has an upright growth habit, whereas the 'KORcaseipp' has a very tall growth habit.
3. 'KORkinteral' has excellent disease resistance, whereas 'KORcaseipp' has good disease resistance.

The new rose plant may be distinguished from its pollen parent, *Rosa hybrida* 'KORpastato', by the following combination of characteristics:

1. 'KORpastato' has a cream white flower color, whereas 'KORcaseipp' has pastel apricot flower color.
2. 'KORpastato' has intense fragrance, whereas 'KORcaseipp' has a very slight fragrance.
3. 'KORpastato' has average disease resistance, whereas 'KORcaseipp' has very good disease resistance.

Comparisons with Similar *Rosa hybrida* Cultivars Known to the Inventor

For a comparison, several physical characteristics of the rose variety 'KORhemtra', a rose variety from the same inventor described and illustrated in U.S. Plant Pat. No. 26,166 are compared to 'KORcaseipp' in Chart 1.

CHART 1

| Characteristic | 'KORcaseipp' | 'KORhemtra' |
|---|---|---|
| General Tonality on Open Flower. | Orange Group 27B. | White Group 155C. |
| Petal Count. | Approximately 130 to 140 petals under normal conditions. | Approximately 50 petals under normal conditions. |
| Average Diameter of the Open Flower. | 90 mm. | 65 to 70 mm. |

That which is claimed:

1. A new and distinct variety of rose plant named 'KORcaseipp', as described and illustrated herein.

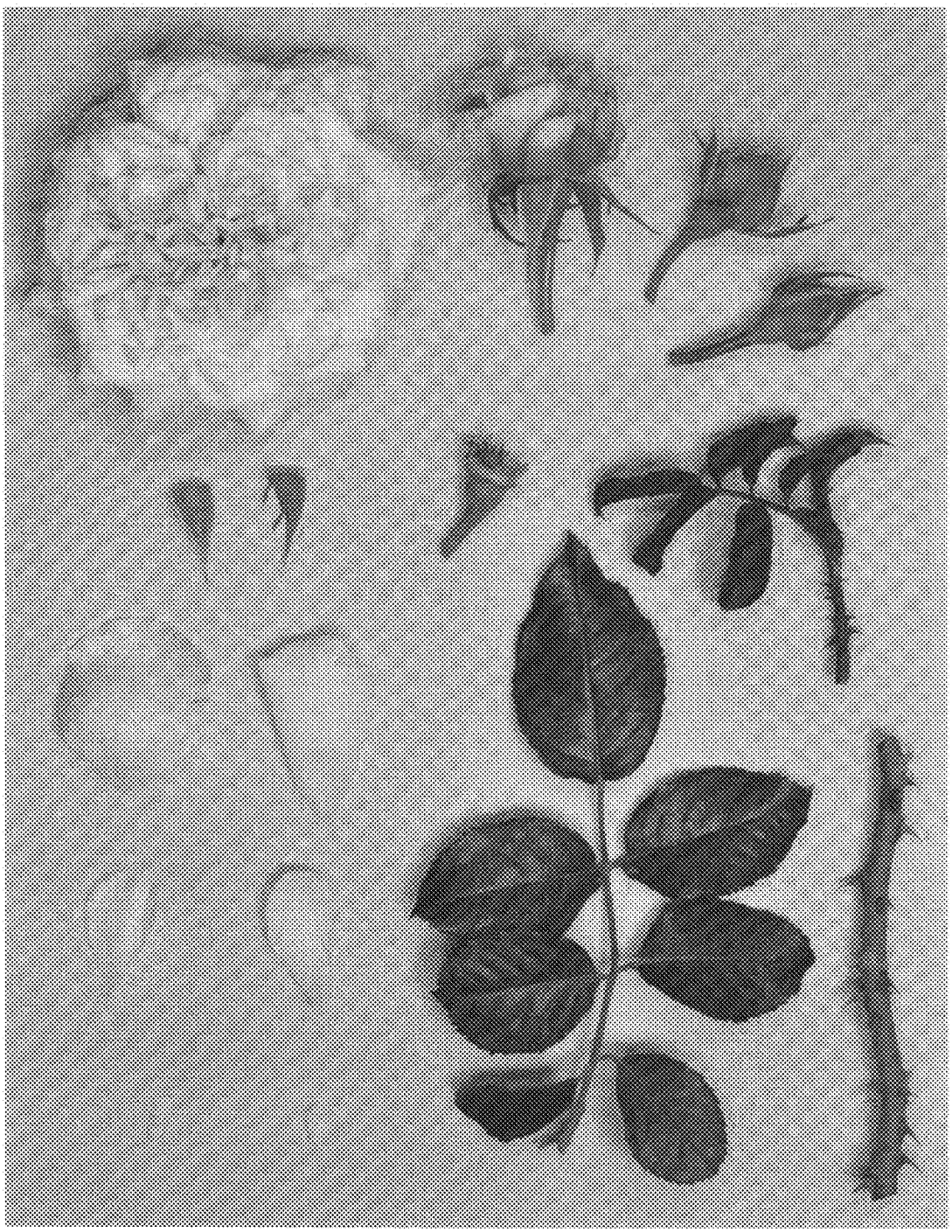

* * * * *